United States Patent [19]

Livaudais, Jr. et al.

[11] 4,201,791

[45] May 6, 1980

[54] PESTICIDE POWDERS, THEIR USE AND PREPARATION

[75] Inventors: Frank B. Livaudais, Jr., 103 Magnolia Dr., Metairie, La. 70005; Joseph W. Spiselman, Brooklyn, N.Y.

[73] Assignee: Frank B. Livaudais, Jr, Metairie, La.

[21] Appl. No.: 837,526

[22] Filed: Sep. 29, 1977

Related U.S. Application Data

[60] Continuation of Ser. No. 722,309, Sep. 10, 1976, abandoned, which is a continuation of Ser. No. 607,347, Aug. 25, 1975, abandoned, which is a division of Ser. No. 376,467, Jul. 5, 1973, abandoned.

[51] Int. Cl.$^2$ ............................................. A01N 9/00
[52] U.S. Cl. .................................... 424/358; 424/200; 424/212; 424/213; 424/216; 424/218; 424/286; 424/352; 424/354; 71/117
[58] Field of Search ............... 424/131, 149, 154, 166, 424/213, 358, 366

[56] References Cited

U.S. PATENT DOCUMENTS 2,967,127 1/1961 Sawyer et al. ...................... 424/358

FOREIGN PATENT DOCUMENTS 376550 6/1962 Japan ........................................ 424/213

OTHER PUBLICATIONS

Chemical Abstracts, vol. 75, (1971), p. 53807y.

*Primary Examiner*—V. D. Turner
*Attorney, Agent, or Firm*—Allegretti, Newitt, Witcoff & McAndrews

[57] ABSTRACT

An at least partially water insoluble powder containing a pesticide in admixture with an inert diluent wherein the pesticide is incorporated within the powder during its formation. The powder can be manufactured by directly admixing the pesticide, i.e., an insecticide, a larvacide, a fungicide, a herbicide, etc., or mixtures thereof, with or without the aid of pre-solution in an organic diluent, into a metalloid or metallic chloride; reacting the resulting mixture in atomized form in a stream of air with an atomized water solution of ammonia or ammoniacal substance in substantially stoichiometric proportion to the chloride to produce a fume; collecting the fume as a powder; and utilizing such activated powder as a pesticide by placing the pesticide below the surface of the earth.

8 Claims, 1 Drawing Figure

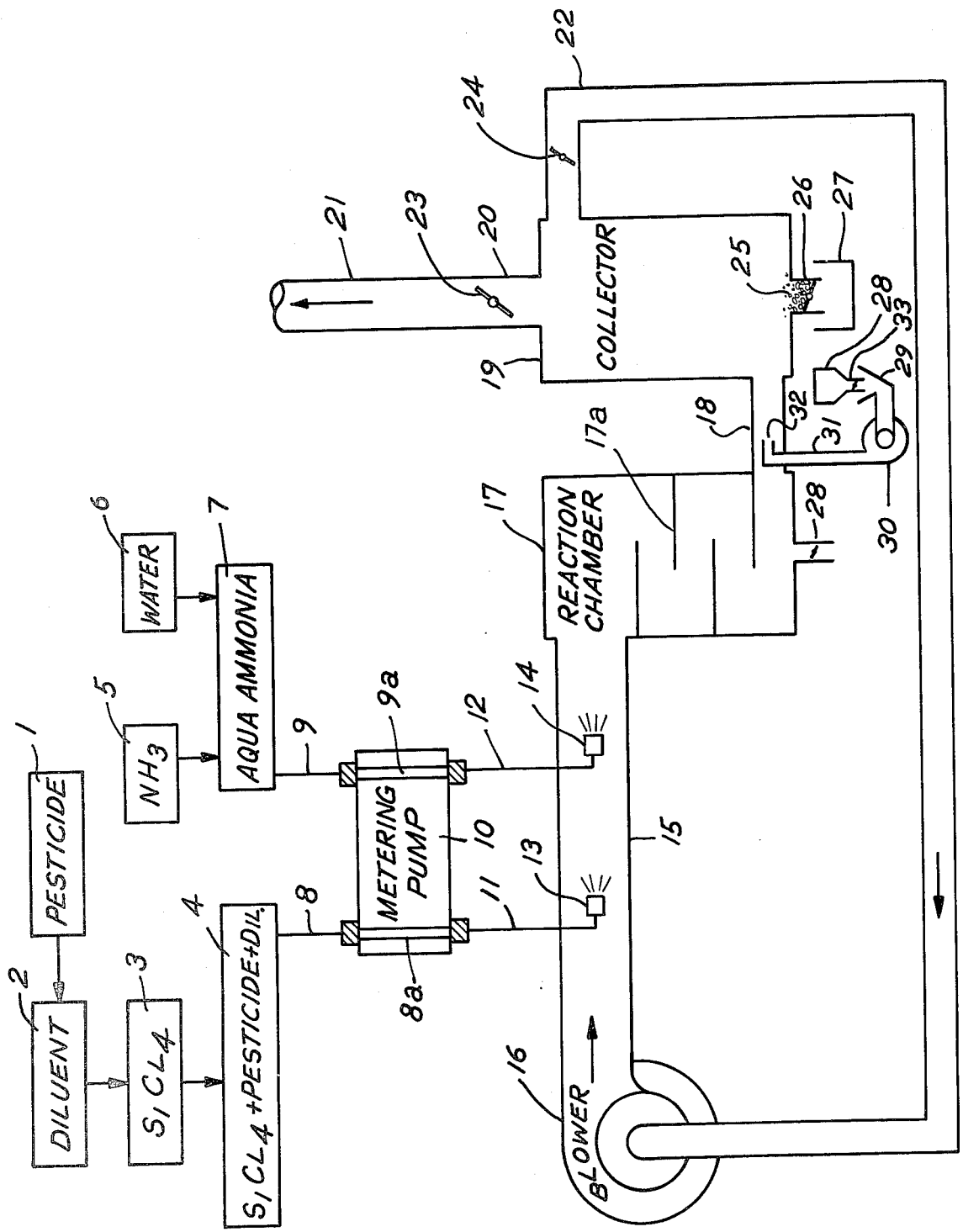

PESTICIDE POWDERS, THEIR USE AND PREPARATION

This is a continuation application of application Ser. No. 722,309, filed On Sept. 10th, 1976 and now abandoned, which is a continuation application of Ser. No. 607,347, filed on Aug. 25th, 1975 and now abandoned, which in turn is a divisional application of Ser. No. 376,467, filed July 5th, 1973 and now abandoned.

BACKGROUND OF THE INVENTION

This invention relates to a pesticide powder wherein the pesticide is released, in a metered fashion, over a prolonged period of time, and an effective method for using this powder.

The admixing of pure pesticides with inert powder for control of insects by subsequently spreading the mixture directly on the ground or by spreading from air-borne vehicles is known. A major disadvantage of admixing pesticide with "inert" powder is the care which must be taken to insure good mixing, particularly when using liquid pesticides, wherein loss of some volatile pesticides can occur. Further, these powders have good initial kill, but have little residual effect when subjected to rain or the flow of ground waters.

Other known systems of distributing pesticides include the spraying of water solutions thereof; the direct atomization of relatively undiluted pesticide in situ in very low volume; and thermal volatization and fuming of a mixture of the pesticide in a "fuel" oil to create a fog. The latter system requires pesticides which are thermally stable.

To obtain a residual effect, pesticides which have an inherent long-time persistence have been used. After many years of use some of these pesticides, such as D D T, are proving to be ecologically undesireable.

Another form of pesticides is illustrated in German Pat. No. 871,981. This patent describes a smoke or mist that is formed by reacting mist forming components which have dissolved therein a pest combating agent. This mist is applied directly to the air as it is formed. The reference fails to recognize that the mist can be collected and used for subsurface or subsequent application.

SUMMARY OF THE INVENTION

For simplicity, in the following specification, the term "pesticide" is used to denote an insecticide, a larvicide, a herbicide, a fungicide, etc., or mixtures thereof which are useful in killing undesirable plant, insect, fungus, etc., growth.

An object of this invention is to provide as a composition of matter a pesticidal powder, which has the pesticide internally bound to its particles such as by absorption, adsorption, occulsion and surface tension in a direct "one-step" reaction phase, in admixture with an inert diluent to provide a controlled dosage method.

Another object of the invention is to provide a process to directly produce a collected pesticidal powder with little or no thermal degradation of the pesticide.

Another object is to provide a method for effectively using pesticidal powder to produce a high initial kill with a protracted residual effect.

Other objects will become apparent in the course of the following specification.

DETAILED DESCRIPTION OF THE INVENTION

The present invention is based in part on the surprising discovery that the powdered particles collected as bulk mass from a chemically produced fog of a pesticide wherein the pesticide is incorporated in the powder during its formation, give an unexpectedly high initial kill when applied directly below the surface of infested ground; and, that its efficacy lasted much longer than that obtained by other methods using the same pesticide.

In addition, the pesticide, (i.e., insecticide or fungicide) can be applied as a coating such as a dust to a seed prior to planting the seed in the ground.

An example, silicon tetrachloride ($SiCl_4$) when atomized into air containing atomized aqua ammonia or ammonia vapor, quickly produces a fog or fume of finely divided solid, dry appearing particles. It has been found that silicon tetrachloride, although a completely inorganic chemical, seemingly dissolves a variety of organic-based pesticides for form a substantially clear solution. This admixture may also be a clear emulsion, or a very stable, non-settling collodial suspension. Apparently no chemical reaction takes place during the mixing, since no rise in temperature, nor evolution of gases, or precipitates were observed. On further experimentation, it was found that for many difficulty soluble pesticides, pre-solution of the pesticide in an organic solvent before admixture with the silicon tetrachloride, effected the formation of a clear solution.

Using a $SiCl_4$-pesticide solution for reaction with ammonia vapor at ambient temperatures as described, a cold fog was produced which exhibited good pesticidal value when collected and used below the surface in an insect infested area. Field tests of subsurface application of the cold fog showed excellent immediate kill (zero count) of insect, and markedly improved average residual effect for the pesticide used.

Samples of the fog were collected as a bulk fluffy powder for application testing by filtration, and settling in still air. These samples were unexpectedly apparently "dry" powders despite the fact that liquid pesticides and diluents had been used in the formulations. On chemical analysis, the pesticide content in the powder were high.

Some of the collected powder was incorporated into larvae infested marshy and swampy ground at a depth of about 1-3 inches and spread on the watery surface in a mosquito infested area. A large reduction in those insects was immediately noted. Days afterward, it was unexpectedly found that the insecticidal and larvicidal effect was still at a high level (i.e., low number of insects present) long after the insect destroying effect that would be obtained by an air-borne fog, or an ultra-low-volume dispersal of the insecticide would have been depleted. Tests showed that the insecticidal value at the ground level was still existant. For example, it was found that the pesticidal effect could be extended from 12-18 hours to 3-4 days or more.

DESCRIPTION OF PREFERRED EMBODIMENT

To more clearly illustrate and describe a preferred method for the production of the powder utilized in the present invention reference is made to the attached schematic flow diagram.

In the FIGURE the pesticide 1, (pre-dissolved in an organic diluent 2 if required to solubilize the pesticide), is added to silicon tetrachloride ($SiCl_4$) 3, to give an admixture of SiCl₄, pesticide, and, if used, diluent 4. Ammonia (NH₃) 5 and water 6 are combined to give a water solution of ammonia (aqua ammonia) 7. Metering pump 10 draws admixture 4 through conduit 8 and into flexible conduit 8a positioned within the pump. Simultaneously, metering pump 10 draws the ammonia solution 7 through conduit 9 and into flexible conduit 9a within the pump. In a preferred embodiment, a commercially available metering pump 10 exerts a common and simultaneously peristaltic action on flexible conduits 8a and 9a thereby forcing the respective liquids into conduits 11 and 12. Conduits 8a and 9a are of a proper, predetermined diameter so that the predetermined quantities delivered by each conduit at each peristaltic stroke yield an ultimate, substantially stoichiometric reaction between the NH₃ and SiCl₄ in the presence of the atomized water. In the preferred embodiment, flexible and squeezable conduits 8a and 9a are removably connected to conduits 8 and 11, and 9 and 12 respectively so that various size conduits 8a and 9a can be used as required and can be discarded when their usefulness ceases. Conduits 11 and 12 lead to spray nozzles 13 and 14 positioned within air-stream conduit 15. Blower 16 propels a stream of air through conduit 15 which picks up the spray and vapors from nozzles 13 and 14. Chemical reaction starts in conduit 15 and is completed in reaction chamber 17 and produces a dense fume of the reaction products. The reaction chamber may be constructed with baffles 17a to knock out any massive liquid droplets and to further promote reaction by turbulence. The fume produced by the chemical reaction is carried by the air stream through conduit 18 to the collector 19 which may be a filter bag unit or an electrical precipitator. In collector 19 the fume is removed from the air stream, and the resultant clear air passes through conduit 20 to stack 21, or preferably through by-pass 22 to be returned to blower 16 for recirculation through the system. The quantity of recirculated air is controlled by dampers 23 and 24 located in stack 21 and by-pass 22 respectively. The collected powder 25 is removed through air lock or valve 26 to container 27. Material that was removed or knocked down in reaction chamber 17 is eliminated through valve or discharge opening 28. One method to quickly and thoroughly dilute and mix the active powder from the reaction chamber 17 with an inert powder is to position container 28, containing an inert powder over air intake 29. Container 28 is directly connected to blower 30, which is connected by air conduit 31 to nozzle 32 positioned in conduit 18. The inert powder, as controlled by valve 33, is fed into the blower, and the resultant stream of air propels the inert powder into the main airstream in conduit 18. The resultant mixture of inert powder and active powder is relatively uniform and ultimately collected in collector 19.

In the apparatus and procedure illustrated quantities of powders may be prepared with many variations in formulations. Pesticides, with and without organic diluents, were admixed with SiCl₄ to form various liquid mixtures. The products of reaction are passed through bag filters and/or an electrical precipitator which collects a fine fluffy, white powder which to all intents and purposes was "dry". In one embodiment, the stream of air is stilled, and the fume settles very slowly to form a fine powder on the surfaces of the stilling or collection chamber.

In any event, the collected powder, when incorporated below the surface of earth containing larvae or insect eggs, will kill or prevent the growth of the eggs or larvae to active insects.

In many instances the quantity of powder required for efficient kill was small in volume. In order to enhance its handling, the active powder is extended by admixture with various inert powders such as precipitated calcium carbonate, ground limestone and diatomaccous earth. The extended powder exhibits the same characteristics and efficiency as unextended powder per given concentration of active powder per area of ground covered.

In one embodiment, a solution of monoethylamine in water is substituted for the stoichiometric quantity of aqua ammonia. The resultant powder contains ethylammonium chloride, and gives substantially the same results as powder produced using aqua ammonia. Similar results may be obtained by substituting an amine or an amine like substance such as morpholine (tetrahydro-1,4 oxazine) for the ammonia. Similarly a water solution of ammonium compound such as ammonium carbonate can be substituted for the stoichiometric equivalent of ammonia required.

In some preparations, titanium tetrachloride may be substituted for SiCl₄ in the formulation. In this embodiment, after the reaction took place, the resultant collected powder acts essentially in the same manner as powder produced using silicon tetrachloride.

The reaction forming the fume due to the interaction of silicon tetrachloride, ammonia and water may be represented as follows:

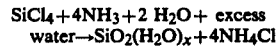

$$SiCl_4 + 4NH_3 + 2 H_2O + \text{excess water} \rightarrow SiO_2(H_2O)_x + 4NH_4Cl$$

The SiO₂ produced is believed to be hydrated, as in silica gel. Much of this reaction takes place in the vapor phase, thus producing a cloud of finely divided hydrated SiO₂ and NH₄ particles. Reaction which takes place within the atomized droplets probably create larger fume particles. A major constituent of the cloud is ammonium chloride. For practical purposes, the respective weights may be considered as above 2 parts by weight of ammonium chloride to one part by weight of non-hydrate SiO₂.

It is believed that, when the pesticide is admixed with the silicon tetrachloride before chemical reaction as above, the reaction in the intimate presence of the pesticide causes the pesticide to be intimately bound to the particles of ammonium chloride and hydrated silicon dioxide such as by occlusion, absorption, adsorption and surface tension. It could be that a larger portion of the pesticide is carried by the silica portion of the powder as by the ammonium chloride despite the opposite ratio of weights, because of the added bulk of the SiO₂ due to its hydration and the known absorptive properties of silica produced by cold chemical reaction. The diluent, if used, acts closely similar to the pesticide.

In this regard, it must be noted that the pesticide must be incorporated into the powder during the formation thereof. If the powder is first made and pesticide then added thereto inferior results are obtained.

It is further theorized that the high immediate kill is the result of the rapidly and easily soluble ammonium chloride quickly releasing the pesticide on first contact with moist earth; and the far longer lasting residual effect comes from the pesticide which is very slowly released from the pores of the insoluble silica gel.

It is also believed that certain very effective pesticides which are normally quickly degraded by earth contact, are protected by enclosing the pesticide in the silica gel, and thus take on a longer effective residual action without the non-degradeable characteristic of some presently frowned upon insecticides such as D D T.

Because of the importance of residual kill, as well as initial kill, the powder produced must be at least partially water insoluble. "At least partially water insoluble," refers to powders that contain a mixture of water soluble and water insoluble components (i.e., $NH_4Cl$ and $SiO_2$) or a powder that has a relatively water insoluble component that will remain intact in the soil for at least 2-3 weeks without dissolving. The powders can include an organic resin having bound therewith pesticides as well as the inorganic compounds mentioned. Further the powders must be microporous to insure controlled metering of the pesticide into the soil.

The invention will be illustrated in greater detail by reference to the following examples which show formulations within the scope of the invention and their method of preparation.

EXAMPLE 1

Three hundred (300) cubic centimeters of $SiCl_4$ are mixed with five hundred (500) cubic centimeters of malathion previously dissolved in two hundred (200) cubic centimeters of kerosene. The resultant mixture is reacted according to the apparatus and process set forth in the attached Figure with three thousand (3000) cubic centimenters of a 6% solution of $NH_3$ in water. The apparatus is operated for approximately 10 minutes during which time the flow of air is approximately 500 cubic feet a minute at a linear velocity of approximately 1000 feet per minute at the spray nozzles; and substantially less in the reaction chamber and in the collecting chamber.

The powder collected weighs over 1000 grams and appears to by "dry".

Approximately 15 grams of the powder are very carefully spotted around on a 40×100 plot of ground heavily infested with insect larvae and adult mosquitos at a depth of 1-6 inches. At the end of 8 hours, a zero count of mosquitos is obtained at the center of the plot. At the end of 48 hours, a sample of the earth is visually larvae-free. The mosquito count is still virtually zero at ground level 6 days later. The earth is essentially larvae free 2 weeks later.

The above 15 grams of powder presents some difficulty in spreading evenly. Accordingly, another 15 grams of the powder are mixed with 1 pound of precipitated calcium carbonate powder to facilitate handling and this mixture is used below the surface on an adjoining plot of equal size. The results obtained on mosquitos and larvae are substantially the same as obtained for the non-extended powder.

Another 15 grams of active powder are mixed with 1 lb. of kieselguhr (diatomaceous earth), and scattered below the surface on still another adjoining plot of equal size. The results on mosquitos and insect larvae are substantially the same as obtained with calcium carbonate.

EXAMPLE 2

One hundred and fifty cubic centimeters of malathion and 150 cubic centimeters of fenthion are mixed with 300 cc of silicon tetrachloride. This mixture is reacted with 3000 cc of 6% ammonia solution and the products of reaction are collected. The amount of air circulated in the apparatus is increased to twice the quantities and velocities, and the rate of feed of the reactants is slowed to one fourth that illustrated in Example 1. The collected powder when used in a field test exhibits the same characteristics as in Example 1.

In the apparatus of the Figure, items 28, 29, 30, 31 and 32 are used in a repetition of the above example to blow approximately 50 pounds of fine diatomaceous earth into the main stream of air and reaction products in conduit 18. The resultant collected mixed powder of active powder and inert diatomaceous earth exhibits the same characteristics as the products of Example 1.

EXAMPLE 3

Zineb (technical grade) is difficult to dissolve in silicon tetrachloride. A solution of 300 grams of zineb in 500 cc of trichloretylene, however, readily dissolves in 300 cc of silicon tetrachloride. Accordingly, this mixture is used in the reaction and process as set forth in Example 1 using 1800 cc of aqua ammonia containing 10% $NH_3$. A portion of the resulting powder is tested on a small patch of ground with results similar to Example 1. Three weeks later, a sample of the soil is still practically larvae free.

EXAMPLE 4

Three hundred (300) cc of a herbicide, 2, 4-D, (2.4,-dichlorophenoxy acetic acid) are dissolved in 300 cc of heavy aromatic spirits. The resulting solution is added to 400 cc of silicon tetrachloride. The reaction and process are carried out as set forth in Example 1 using 2000 cc of ammonium carbonate water solution containing the equivalent of 12% $NH_3$. After collection, the resulting powder is used below the surface on a plot having a considerable growth of broad-leaved plants, within a week, the broad-leaved plants are destroyed, and no regrowth is apparent for seven weeks thereafter.

Other examples similar to those noted above, are made using various insecticides, fungicides, larvicides and herbicides, with and without presolution in organic solvents, and with and without dilution of the active powder with inert powders. The examples are on both laboratory and semi-field scale.

The efficacy of the collected products of reaction is so great in many cases that the quantity required for relatively large areas of ground is very small. To improve the handling and non-caking qualities of the powder and to facilitate the spreading thereof the active powder is diluted or extended by admixing with an inert powder such as precipitated calcium carbonate, ground limestone, dry plaster of paris, diatomaceous earth, etc; with results that will compare to results obtainable in the field and laboratory with a proportionate amount of non-extended active powder.

The ammoniacal reactants are variously water solutions of ammonia (aqua ammonia) ranging from 2% $NH_3$ to commercial available 26% $NH_3$. Best results appeared to be obtained with 5% to 12% solutions. Similarly in some tests, a solution of technical grade ammonium carbonate is substituted for equivalent moles of ammonia. In other tests, ammonia gas is introduced into the air stream simultaneously with an adjacent spray of water. Good reactions took place, but are, with the apparatus used, more difficult to control. In a number of tests, organic materials of an amine nature such as mono diethylamine or morpholine dissolved in water, are used in proportional quantities (mole) in place of ammonia.

Analysis of active powders shows a good recovery of the original quantity of pesticide used as based on the percentage recovery of the products of the reaction.

Recovery of the products of reaction, that is, the collection of the active powder, can be achieved by means of settling in still air, by filtration media such as filter bag equipment, and by electrical precipitation. In some cases, it is found that the dryness of the powder and its non-caking qualities are enhanced by carrying out the process in a slightly heated air stream.

Examples of some of the various insecticides, larvicides, fungicides, herbicides, etc., and the formulations that can be used for reactant 4 in the process illustrated in the Figure are enumerated below. In these formulations and other used, the insecticides, etc., were generally of technical or commercial grade and are referred to in most cases by their well-known trade names for simplicity. For example, the trade name "Malathion" refers to [(S-1,2bis(ethoxycarboayl)ethyl-O,O-dimethyl phosphorodithioate]; "Nankor-8" is O,O-dimethylol O-2,4,5 trichlorophenyl phosphorosulphonate; D D T is dichloro diphenyl trichloroethane; Cidial is ethyl ester of Acid O, odimethyldithiophosphoril-1-sonil acetate; etc.. The chemical formulas corresponding to various trade-name pesticides are well known to those trained in the art.

Examples of Reactant 4 of the FIGURE (1)
250 cc Nankor-8
200 cc Kerosene
350 cc $SiCl_4$ (2)
600 cc Malathion
400 cc $SiCl_4$ (3)
600 cc Chlordane
100 cc Kerosene
300 cc $SiCl_4$ (4)
200 gr Dieldrin
450 cc Benzene
350 cc $SiCl_4$ (5)
250 gr D D T
500 cc heavy aromatic spirits
300 cc $SiCl_4$ (6)
250 gr Lindane
500 cc Trichloroethylene
300 cc $SiCl_4$ (7)
300 cc Chlordane
150 gr Lindane
500 cc $SiCl_4$ (8)
700 cc Cidial
300 cc $SiCl_4$ (9)
200 gr Endrin
500 cc Benzine
300 cc $SiCl_4$

(10)
500 cc Dursban
500 cc $SiCl_4$

(11)
400 cc Parathion
500 cc $SiCl_4$

Other formulations besides those given as examples above are used. The pesticides are used separately in the formulation with silicon tetrachloride, or in various combinations to obtain combined effects.

In a series of other tests, an equivalent mole proportion of titanium tetrachloride is substituted for the $SiCl_4$ in a number of formulations. The process of making the active powder is then followed using a stoichiometric amount of 10% ammonia. A powder is produced which exhibited larvicidal and insecticidal properties to a considerable degree. In one test, the same technique is used with stannic tetrachloride with similar results. In two tests a water solution of aluminum sulphate is admixed with water soluble pesticide such as Fundal or Carzol and reacted with ammonia gas using extremely fine sprays and heated air in the apparatus. A good fog is produced. The bulky powder collected shows the presence of aluminum oxide (probably hydrated), ammonium sulphate and larvicide. The powder exhibited larvicidal and residual properties to a high degree. A similar experiment with an iron chloride solution plus pesticide yields essentially equivalent results.

The examples given above are by way of illustration to show the many variations and modifications within the scope of this invention, but not in way of limitation.

We claim as our invention:

1. A method for producing a pesticidal composition of matter which comprises:

(a) passing a first stream comprising aluminum sulfate in aqueous solution, a metallic chloride or silicon tetrachloride to a first conduit;

(b) passing a second stream comprising ammonia, an amine, or an ammonium compound in water in substantially stoichiometric amount to said first conduit;

(c) admixing a compound or compounds selected from the group consisting of an insecticide, a larvicide and a fungicide with one of said first or second streams;

(d) passing a third stream comprising air through said conduit to contact said first stream and said second stream;

(e) passing the resultant mixture to a reaction chamber maintained near ambient temperature;

(f) passing the resultant reaction mixture to a separation chamber; and (g) removing said pesticidal composition from said separation chamber.

2. A method as in claim 1 wherein said first stream is silicon tetrachloride or titanium tetrachloride and said second stream is ammonia in water.

3. A method as in claim 1 wherein said compound or compounds selected from the group consisting of an insecticide, a larvicide and a fungicide is dissolved in said first stream.

4. A method as in 3 wherein said compound or compounds selected from the group consisting of an insecticide, a larvicide and a fungicide is first dissolved in an organic solvent before admixture with said first stream.

5. A method for producing a pesticidal composition which comprises:

(a) passing a first stream comprising silicon tetrachloride, titanium tetrachloride, tin tetrachloride, iron chloride in aqueous solution or aluminum sulfate in aqueous solution to a first conduit;

(b) passing a second stream comprising a water solution of ammonia, monoethylamine, morpholine, ammonium carbonate or ammonia gas and water spray in a substantially stoichiometric amount to said first conduit;

(c) admixing a compound or compounds selected from the group consisting of an insecticide, a larvicide and a fungicide with one of said first or second streams;

(d) passing a third stream comprising air through said conduit to contact said first stream and said second stream;

(e) passing the resultant mixture to a reaction chamber maintained near ambient temperature;

(f) passing the resultant reaction mixture to a separation chamber;

(g) removing said pesticidal composition from said separation chamber by means of settling, filtration or electrical precipitation; and (h) removing air from said separation chamber and recycling at least a portion of said air to said first conduit.

6. A method as in claim 5 wherein said compound or compounds selected from the group consisting of an insecticide, a larvicide and a fungicide is dissolved in said first stream.

7. A method as in claim 5 wherein said compound or compounds selected from the group consisting of an insecticide, a larvicide and a fungicide is first admixed with an organic solvent selected from the group consisting of trichloroethylene, heavy aromatic spirits, kerosene and benzene, before admixture with said first stream.

8. A method as in claim 5 wherein a fourth stream comprising an inert extender of calcium carbonate, diatomaceous earth, ground limestone or dry plaster of paris is admixed with said reaction mixture prior to its passing to the separation chamber.

* * * * *